United States Patent
Kazama et al.

[11] Patent Number: 6,070,092
[45] Date of Patent: May 30, 2000

[54] METHOD AND APPARATUS FOR MEASURING OPTICAL PROPERTIES OF SURFACE STATE OF SKIN

[75] Inventors: Haruhito Kazama; Yoshinao Nagashima; Yukihiro Yada, all of Tokyo, Japan

[73] Assignee: Kao Corporation, Tokyo, Japan

[21] Appl. No.: 09/176,026

[22] Filed: Oct. 21, 1998

[51] Int. Cl.[7] ...................................................... A61B 5/00
[52] U.S. Cl. ........................ 600/310; 600/473; 600/476
[58] Field of Search .................................. 600/310, 315, 600/322, 323, 340, 473, 476

[56] References Cited

U.S. PATENT DOCUMENTS 5,524,617   6/1996   Mannheimer ............................ 600/323
5,671,735   9/1997   Macfarlane et al. ..................... 356/405

FOREIGN PATENT DOCUMENTS 335343   7/1998   Taiwan .

*Primary Examiner*—Eric F. Winakur
*Attorney, Agent, or Firm*—Oblon, Spivak, McClelland, Maier & Neustadt, P.C.

[57] ABSTRACT

Light Lo is allowed to be applied on the skin S, the internal scattered light Li in the region from the surface of the skin S to the microcirculation system is detected preferably in at least three wavelength regions of 400 to nm, 500 to 600 nm, 600 to 800 nm, or 800 to 1500 nm, and the optical properties which are affected by blood circulation, such as skin color, spots, and discoloration are determined. With these optical properties, the surface state of the skin can be evaluated better.

12 Claims, 6 Drawing Sheets

METHOD AND APPARATUS FOR MEASURING OPTICAL PROPERTIES OF SURFACE STATE OF SKIN

BACKGROUND OF THE INVENTION

1. Field of the Invention

The present invention relates to a method for measuring the optical properties in the region from the skin surface to the microcirculation system which is affected by hemoglobin, melanin, and the like, and of thereby measuring the surface state of the skin.

2. Description of the Related Art

Methods known in the past as methods for measuring and evaluating skin pigmentation, discoloration, and the like include the method in which light having a specific wavelength is allowed to be incident on the skin surface, the reflected light is received, and the skin reflectance at a specific wavelength is determined, thereby allowing erythema or pigmentation to be evaluated (Japanese Unexamined Patent Application 58-33153). In another known method for measuring skin pigmentation, the ratio of reflectance on the skin at two specific wavelengths is measured, so as to determine the index relating to the melanin content or hemoglobin content (Japanese Unexamined Patent Application 5-161609).

Yet another known method for measuring the epidermal hue that are unaffected by blood is the method in which the skin surface is drawn and partially pulled up, white light is allowed to be incident on that part, and the spectral spectrum of the transmitted light on the epidermal is determined (Japanese Unexamined Patent Application 5-87730).

Problems in the aforementioned methods for measuring the reflected light on skin, however, are that the light which is received includes a great deal of surface scattered light in addition to internal scattered light in the skin, resulting in significant variation in the optical path length of the received light, which makes accurate analysis impossible.

Problems in the method for detecting transmitted light on the epidermal are that the detected results are not affected by blood, making it impossible to evaluate the degree of skin color affected by blood circulation.

An object of the present invention is to resolve the aforementioned disadvantages of the conventional technology, allowing better evaluation of the optical properties of skin, such as discoloration and shading in which the microcirculation of the blood and melanin deposition are involved.

SUMMARY OF THE INVENTION

The inventors of the present invention have found that the aforementioned object can be achieved by detecting the internal scattered light in skin when the subject of measurement is the region from the skin surface to the microcirculation system.

That is, the present invention provides a method for measuring the optical properties of the surface state of skin comprising applying light on the skin, detecting the internal scattered light in the region from the skin surface to the microcirculation system and determining the optical properties.

The present invention is particularly intended to provide a method for measuring the surface state of the skin, wherein light is allowed to be applied on the skin in at least three mutually differing wavelengths in the wavelength region between 400 and 1500 nm, especially in three mutually differing wavelengths of 400 to 500 nm, 500 to 600 nm, 600 to 800 nm, and 800 to 1500 nm, respectively, so as to determine the optical properties.

An apparatus for implementing these methods is also provided in the present invention, wherein an apparatus for measuring the surface state of the skin comprises light-projecting means for allowing light having a specific wavelength region to be applied on the skin, light-receiving means for receiving the internal scattered light of the light applied on the skin from the light-projecting means, computing means for computing the optical properties of the skin in the region from the skin surface to the microcirculation system based on the wavelength and amount of light received by the light-receiving means, the surfaces of the light-projecting means and light-receiving means facing the skin being surrounded by a 0.2 to 0.8 mm high peripheral wall.

According to the present invention, the internal scattered light in the region from the skin surface to the microcirculation system is detected, making it possible to better detect, for example, the hemoglobin of the microcirculation system and the melanin which occurs in the stratum corneum of the skin and causes skin pigmentation. It is thus possible to better evaluate the surface state of the skin, such as skin discoloration, the degree of skin color reflecting blood circulation, and the like.

Internal scattered light, not surface scattered light, is detected according to the present invention, resulting in a better S/N ratio and less variation in the optical path length of the detected light.

In the present invention, the microcirculation system of the skin refers to the blood flow system in the region between the capillaries and tissue, which is the blood flow system having the lowest absorption component accompanied with the pulse, with a value of no more than 5% relative to the total absorbance (the total of the absorbance of the tissue, the absorbance of the venous blood of the capillaries, and the absorbance of the arterial blood accompanied with the pulse).

The degree of skin color affected by the blood circulation can be evaluated when the subject of measurement is the microcirculation system, in which the absorption component accompanied with the pulse is no more than 5%, as in the present invention. In contrast, when the main subject of measurement is the absorption component accompanied with the pulse (arterial blood), and not the blood flow located in the extremely shallow regions where skin color is affected, the optical properties of deep blood are detected, making it impossible to measure the color of the skin that is affected by the circulation of the blood.

DESCRIPTION OF THE PREFERRED EMBODIMENTS

The method and apparatus of the present invention are described in detail below with reference to figures. Symbols that are the same in the figures represent the same or equivalent structural elements.

Figure 1:
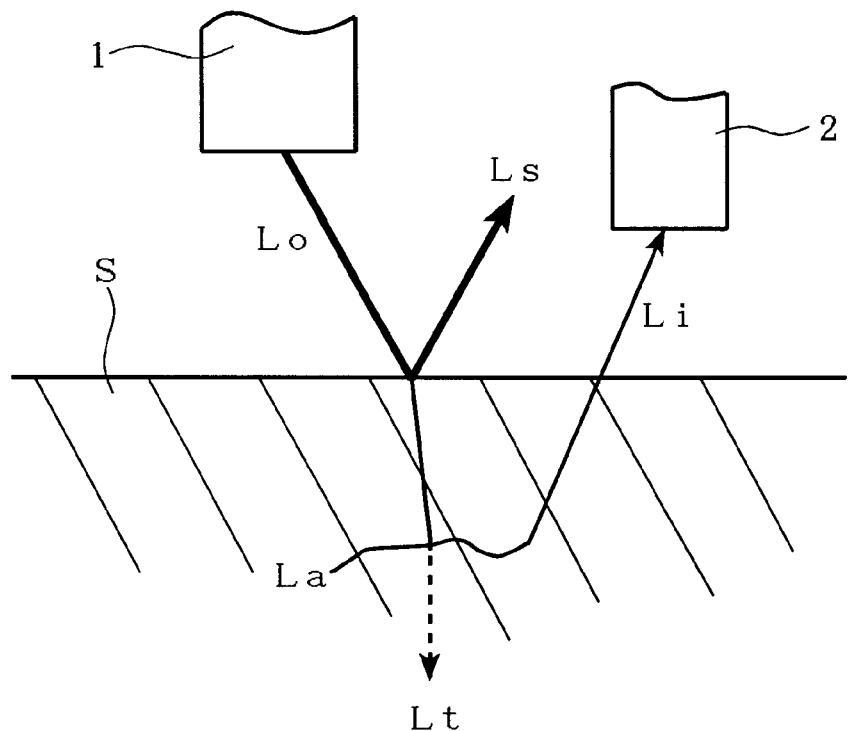
FIG. 1 illustrates the principles of measurement in the method of the present invention.

FIG. 1 illustrates the principles of measurement in the method of the present invention. As shown in the figure, when light Lo from the light-projecting means 1 is allowed to be incident on the skin S, the incident light Lo is divided into surface scattered light Ls and light incident on the interior of the skin S, and the light incident on the interior of the skin is divided into light Lt transmitted in the direction of the hypodermis, absorbed light La, and light Li which is internal scattered light emitted from the skin surface. When the light Lo incident on the skin S is visible light, there is little transmitted light Lt in the tissue below the hypodermis, making the transmitted light Lt relatively negligible compared to the amount of surface scattered light Ls, internal scattered light Li, or absorbed light La. The following approximation is thus possible.

amount of incident light=amount of surface scattered light+amount of internal scattered light+amount of absorbed light The internal scattered light and absorbed light can be considered to have information based on pigments in the skin because the wavelength distribution and amount of light each correspondingly vary as a result of the pigment absorption wavelength in the skin and the pigment concentration.

When the measuring system is constructed in such a way that the surface scattered light in the aforementioned equation can be disregarded or in such a way that it can be handled as noise, the Lambert-Beer principle can be applied to the amount of incident light and the internal scattered light, and can be represented as shown below.

$$\log(I_o/I_s) = \epsilon c l$$

(where $I_o$: amount of incident light; $I_s$: amount of internal scattered light; $\epsilon$: pigment absorption coefficient; c: pigment concentration; and l: optical path length.)

Figure 2:
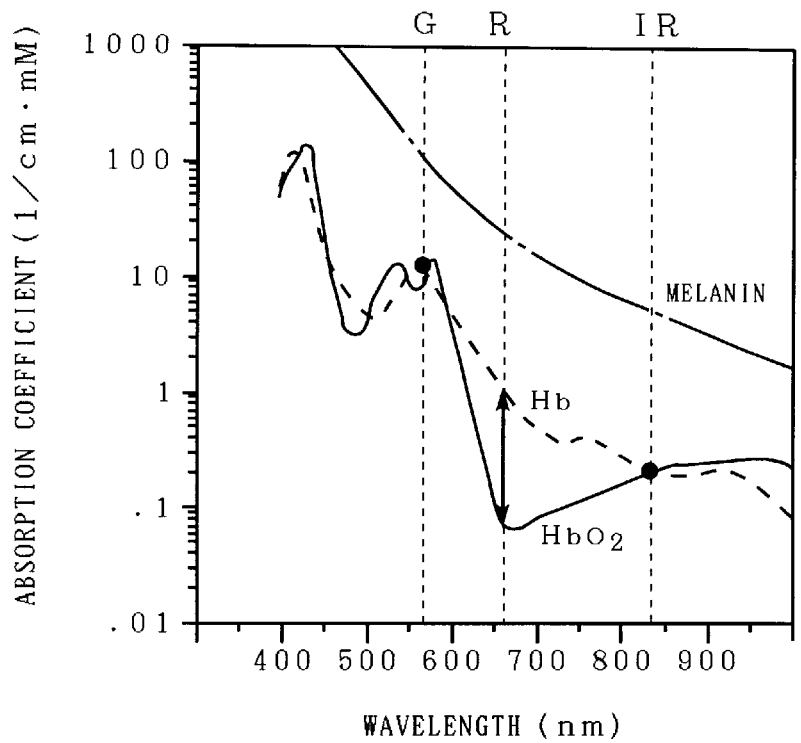
FIG. 2 shows the absorption spectra for melanin, oxygenated hemoglobin ($HbO_2$), and reduced hemoglobin (Hb)

Examples of pigments in the skin affecting the internal scattered light are the melanin primarily present in the epidermis and hemoglobin primarily present in the hypodermis, which occurs in oxygenated form ($HbO_2$) and reduced form (Hb). These pigments have characteristic absorption spectra, as shown in FIG. 2. The effects of skin cells and tissue on the internal scattered light are negligible.

The internal scattered light of the skin can accordingly be detected to determine the concentration of pigments such as hemoglobin and melanin in the skin.

For example, in FIG. 2, the absorption coefficients for oxygenated hemoglobin and reduced hemoglobin at wavelengths 565 nm (G) and 830 nm (IR) are equivalent, allowing the calculations for determining the pigment concentrations from the absorbance of the detected light to be simplified. The ratio between the absorption coefficients of oxygenated hemoglobin ($HbO_2$) and reduced hemoglobin (Hb) is greatest at a wavelength of 660 nm, so the oxygen saturation of hemoglobin can be calculated by comparison of the absorbance values at the wavelengths where the absorption coefficients of the aforementioned oxygenated hemoglobin and reduced hemoglobin are equivalent (565 nm, 830 nm). The concentration of the pigments is determined in consideration of the effect of the pigments on the absorbance values of these three wavelengths, where the absorbance values at the three wavelengths 565 nm (G), 830 nm (IR), and 660 nm (R) are $A_G$, $A_{IR}$, and $A_R$.

In this case, the melanin and hemoglobin are present in the epidermis and hypodermis, respectively, where the epidermis thickness is $d_D$ and that of the hypodermis is $d_E$.

$$d_D = k d_E \text{ (where k is the coefficient)}$$

This can be expressed depending on the distance of the transmitted depth at wavelengths G, IR, and R.

$$d_{(R)} = m \cdot d_{(G)} \text{ and } d_{(IR)} = n \cdot d_{(G)}$$

This relationship is true in the hypodermis represented by the letter D and the epidermis represented by the letter E.

Hence, the three aforementioned absorbance values $A_G$, $A_{IR}$, and $A_R$ are represented as shown in the following Equations (1) through (3). In the equations, $\epsilon_{X(Y)}$ represents the absorption coefficient for X at wavelength Y, and $C_x$ represents the concentration of X.

$$\begin{aligned}
d_{D(G)} &= k \cdot d_{E(G)} \\
A_G &= A_{HbO2(G)} + A_{Hb(G)} + A_{M(G)} \\
&= \varepsilon_{HbO2(G)} \cdot C_{HbO2} \cdot d_{D(G)} + \varepsilon_{Hb(G)} \cdot C_{Hb} \cdot d_{D(G)} + \\
&\quad \varepsilon_{M(G)} \cdot C_M \cdot d_{E(G)} \\
&= \varepsilon_{HbO2(G)} \cdot (C_{HbO2} + C_{Hb}) \cdot k \cdot d_{E(G)} + \varepsilon_{M(G)} \cdot C_M \cdot d_{E(G)} \\
&= (k \cdot \varepsilon_{HbO2(G)} \cdot C_{THB} + \varepsilon_{M(G)} \cdot C_M) \cdot d_{E(G)}
\end{aligned} \quad (1)$$

$$\begin{aligned}
d_{E(IR)} &= n \cdot d_{E(G)}, \, d_{D(IR)} = k \cdot n \cdot d_{E(G)} \\
A_{IR} &= A_{HbO2(IR)} + A_{Hb(IR)} + A_{M(IR)} \\
&= \varepsilon_{HbO2(IR)} \cdot C_{HbO2} \cdot d_{D(IR)} + \varepsilon_{Hb(IR)} \cdot C_{Hb} \cdot d_{D(IR)} + \\
&\quad \varepsilon_{M(IR)} \cdot C_M \cdot d_{E(IR)} \\
&= \varepsilon_{HbO2(IR)} \cdot (C_{HbO2} + C_{Hb}) \cdot k \cdot n \cdot d_{E(G)} + \\
&\quad \varepsilon_{M(IR)} \cdot C_M \cdot n \cdot d_{E(G)} \\
&= (k \cdot n \cdot \varepsilon_{HbO2(IR)} \cdot C_{THB} + n \cdot \varepsilon_{M(IR)} \cdot C_M) \cdot d_{E(G)}
\end{aligned} \quad (2)$$

$$\begin{aligned}
d_{E(R)} &= m \cdot d_{E(G)}, \, d_{D(R)} = k \cdot m \cdot d_{E(G)} \\
A_R &= A_{HbO2(R)} + A_{Hb(R)} + A_{M(R)} \\
&= \varepsilon_{HbO2(R)} \cdot C_{HbO2} \cdot d_{D(R)} + \varepsilon_{Hb(R)} \cdot C_{Hb} \cdot d_{D(R)} + \\
&\quad \varepsilon_{M(R)} \cdot C_M \cdot d_{E(R)} \\
&= \varepsilon_{HbO2(R)} \cdot C_{HbO2} \cdot k \cdot m \cdot d_{E(G)} + \varepsilon_{Hb(R)} \cdot \\
&\quad C_{Hb} \cdot k \cdot m \cdot d_{E(G)} + \varepsilon_{M(R)} \cdot C_M \cdot m \cdot d_{E(G)} \\
&= (k \cdot m \cdot \varepsilon_{HbO2(R)} \cdot C_{HbO2} + k \cdot m \cdot \varepsilon_{Hb(R)} \cdot C_{Hb} + \\
&\quad m \cdot \varepsilon_{M(R)} \cdot C_M) \cdot d_{E(G)}
\end{aligned} \quad (3)$$

Hence, from Equations (1) through (3), the oxygenated hemoglobin concentration $C_{HbO2}$, reduced hemoglobin concentration $C_{Hb}$, and melanin concentration $C_M$ are obtained, which can be expressed as shown in the following Equations (4) through (6).

$$C_{HbO2} \cdot d = \frac{(\varepsilon_{HbO2(IR)} \cdot \varepsilon_{M(R)} - \varepsilon_{Hb(R)} \cdot \varepsilon_{M(IR)}) A_G +}{k \cdot (\varepsilon_{HbO2(R)} - \varepsilon_{Hb(R)})} \quad (4)$$

$$= \frac{\dfrac{-10500 A_G - 1390000/n \cdot A_{IR}}{554000} + 1/m \cdot A_R}{-11.8 \cdot k} =$$

$$\dfrac{\dfrac{105 A_G + 13900/n \cdot A_{IR}}{5540} - 1/m \cdot A_R}{11.8 \cdot k}$$

$$C_{Hb} \cdot d = \frac{(\varepsilon_{HbO2(R)} \cdot \varepsilon_{M(IR)} - \varepsilon_{HbO2(IR)} \cdot \varepsilon_{M(R)}) A_G +}{k \cdot (\varepsilon_{HbO2(R)} - \varepsilon_{Hb(R)})} \quad (5)$$

$$= \frac{\dfrac{-26000 A_G + 1540000/n \cdot A_{IR}}{554000} - 1/m \cdot A_R}{-11.8 \cdot k} =$$

$$\dfrac{\dfrac{260 A_G - 15400/n \cdot A_{IR}}{5540} + 1/m \cdot A_R}{11.8 \cdot k}$$

$$C_M \cdot d = \frac{1/n \cdot \varepsilon_{HbO2(G)} \cdot A_{IR} - \varepsilon_{HbO2(IR)} \cdot A_G}{(\varepsilon_{HbO2(G)} \cdot \varepsilon_{M(IR)} - \varepsilon_{HbO2(IR)} \cdot \varepsilon_{M(G)})} \quad (6)$$

$$= \frac{195/n \cdot A_{IR} - 3.77 A_G}{554000}$$

Then, to determine absorbance values $A_G$, $A_{IR}$ and $A_R$ makes it possible to calculate the oxygenated hemoglobin concentration $C_{HbO2}$, reduced hemoglobin concentration $C_{Hb}$, and melanin concentration $C_M$.

According to the present invention, it is thus possible to determine the oxygenated hemoglobin concentration C2 and reduced hemoglobin concentration $C_{Hb}$, as well as the ratio between the oxygenated hemoglobin concentration $C_{HbO2}$ and reduced hemoglobin concentration $C_{Hb}$, allowing the effects of blood flow on skin color to be evaluated in more detail. Here, the ratio between the oxygenated hemoglobin concentration $C_{HbO2}$ and reduced hemoglobin concentration $C_{Hb}$ is the oxygen saturation, that is, the proportion in which the hemoglobin is bonded to oxygen. The state of melanin pigmentation can be accurately evaluated.

Figure 3:
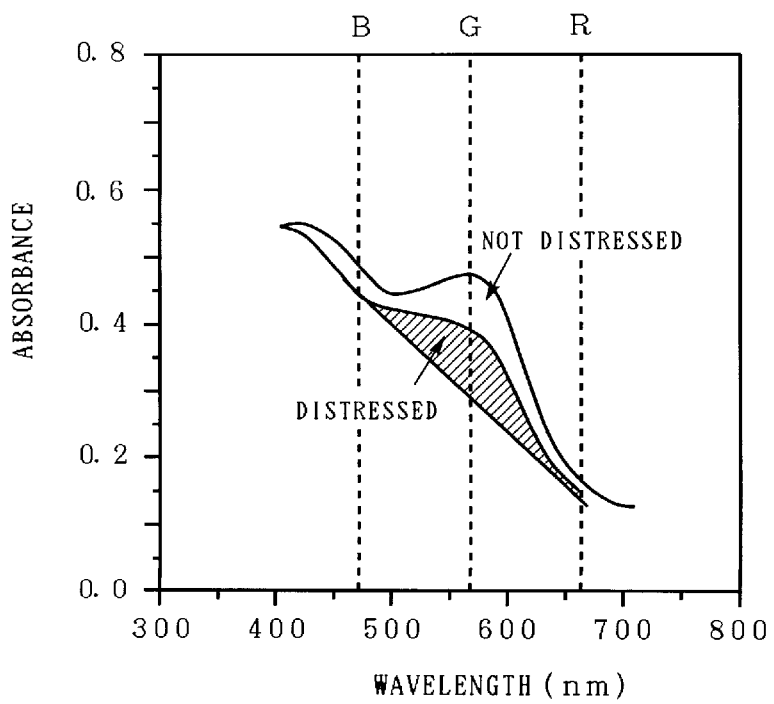
FIG. 3 is an illustration of the spectral properties of distressed skin color.

FIG. 3 is an illustration of the spectral properties of distressed skin color, summarizing the presence or absence of discoloration (that is, the presence or absence of skin distress) and the spectral properties of the skin absorbance of patients when the skin color of the patients (30 patients ranging in age from 20 to 50 years) was visually classified by a panel of experts as being discolored (N=17) or not discolored (N=14). As shown in the figure, skin distress is evaluated according to the magnitude of the absorption peaks around wavelengths 500 to 600 nm (R). This is attributed to the fact that individuals with an abundance of total hemoglobin in the blood have good blood flow, resulting in a healthy, ruddy skin color, whereas individuals with low total hemoglobin have poor blood flow, resulting in a bluish skin tone.

The present invention thus allows the degree of skin color related to hemoglobin to be evaluated in terms of "skin color index", which is a simpler index of evaluation. That is, the skin color index corresponds to the surface area of the slope in FIG. 3, and is expressed by the following equation.

Skin Color index=

½×(absorbance (470 nm) of B+absorbance (565 nm) of G)×(565+ 470)+½×(absorbance (565 nm) of G+absorbance (660 nm)

of R)×(660+565)+½×(absorbance (470 nm) of B+absorbance (660nm) of R)×(660+470)=⁹⁵⁄₂×(absorbance (470 nm) of B+2× (absorbance (565 nm) of G+absorbance (660 nm) of R)

The present invention also involves the method for evaluating the degree of skin color using this skin color index.

In the method described above, the internal scattered light in the skin was received and evaluated using three wavelengths, but the present invention is not limited to this method. The detected wavelengths can be determined as needed according to the light source, light sensor, and the like. For example, any wavelengths between 400 and 1500 nm can be used, such as wavelengths in the B region of 400 to 500 nm including the wavelength at which the absorption coefficients for oxygenated and reduced hemoglobin are equivalent, wavelengths in the G region of 500 to 600 nm at which the sensitivity of oxygenated and reduced hemoglobin is greatest, wavelengths in the R region of 600 to 800 nm including the wavelength at which the absorption coefficients for oxygenated and reduced hemoglobin are equivalent, and wavelengths in the IR region of 800 to 1500 nm.

However, in cases where three types of pigments are involved in the detection wavelength, three or more wavelength regions are preferably selected from the aforementioned wavelength regions.

Figure 4A:
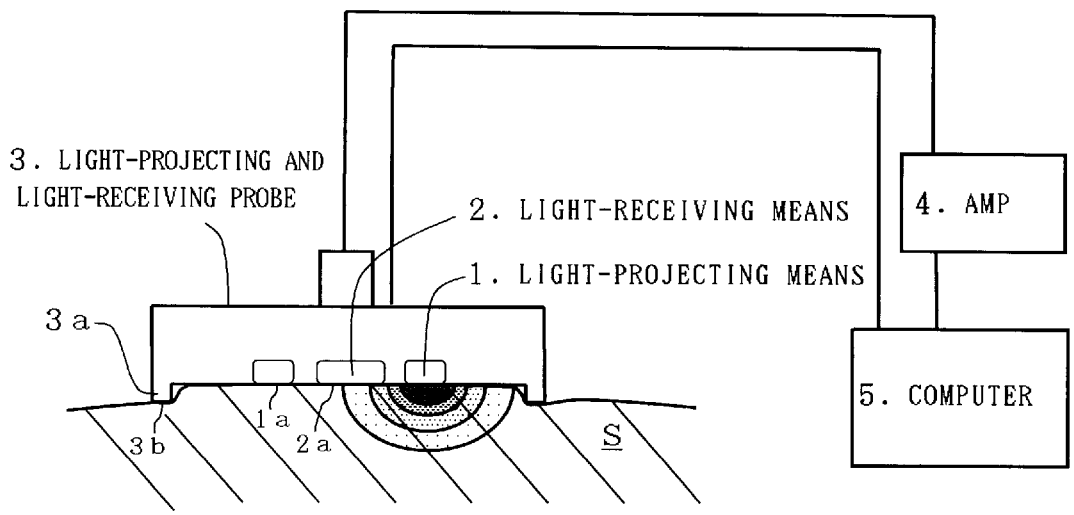
FIG. 4 is a schematic structural diagram of an example of the apparatus in the present invention (FIG. 4A) and a bottom view of the light-projecting and light-receiving probe therein (FIG. 4B)
Figure 4B:
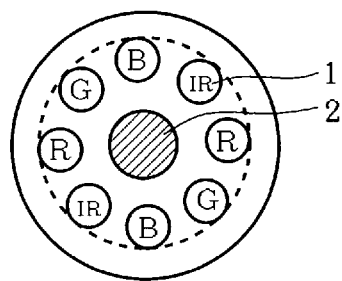

FIG. 4 is a schematic structural diagram of an example of the apparatus in the present invention for detecting internal scattered light in the region from the skin surface to the microcirculation system to determine the optical properties (FIG. 4A), and a bottom view of the light-projecting and light-receiving probe therein (FIG. 4B).

Figure 5:
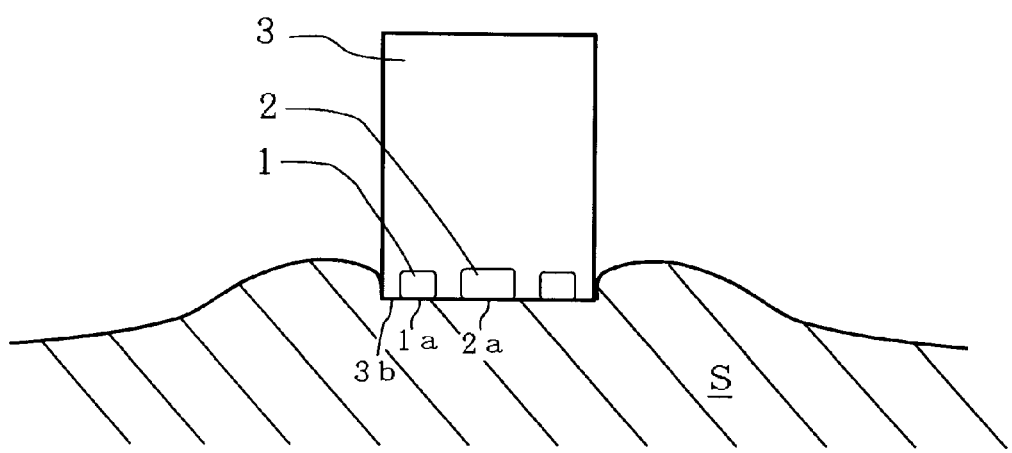
FIG. 5 illustrates the use of an example of an apparatus different from that of the present invention.

The apparatus in the figure comprises a light-projecting and light-receiving probe 3 integrally incorporating light-projecting means 1 that is brought into contact with the skin S to allow light of a specific wavelength to be incident thereon, and light-receiving means 2 for receiving the internal scattered light from the light-projecting means 1 incident on the skin S; an amp 4 for amplifying detection signals for the light received by the light-receiving means 2; and a computer 5 for computing the optical properties of the skin S from the wavelength and amount of the light that is detected. This apparatus is characterized in that the surface 1a of the light-projecting means 1 facing the skin S and the surface 2a of the light-receiving means 2 facing the skin S in the light-projecting and light-receiving probe 3 are surrounded by a peripheral wall 3a that is 0.2 to 0.8 mm high and is formed as an extension of the outer tube of the light-projecting and light-receiving probe 3. The edge 3b of the peripheral wall 3a of the light-projecting and light-receiving probe 3 is brought into contact with the skin S during the measurements described below, yet no blood is excluded from the microcirculation system at the measuring location of the skin S by the pressure of the light-projecting means 1 or light-receiving means 2 at that location, so that it is possible to prevent decreases in the absorption based on the hemoglobin during measurement. Contrary to this, the light-projecting and light-receiving probe 3 as shown in FIG. 5 is not preferable. The skin S at the measuring location will be pressed when the light-projecting and light-receiving probe 3 is brought into contact with the skin S, the blood in the microcirculation system at that location will be excluded from, and it will not be possible to accurately measure the inherent state of the skin. Accordingly, the surface 1a of the light-projecting means 1 facing the skin S and the surface 2a of the light-receiving means 2 facing the skin S should not be formed on the same plane as the edge 3b of the outer tube of the light-projecting and light-receiving probe 3.

In the apparatus illustrated in FIG. 4, the light-projecting means 1 comprises four kinds of light-emitting diodes (their light-emitting wavelengths are B (470 nm), G (565 nm), R (660 nm), and IR (830 nm), respectively ) which are concentrically disposed about the light-receiving means 2. To minimize error due to the direction of the projected light, at least two light-emitting diodes for each color should be provided.

The light-receiving means 2 comprises a photodiode. Although the light-receiving means 2 in the figure consists of a single photodiode, a plurality of photodiodes may be used as needed to improve detection precision.

The distance L between the center of light-projecting means 1 and the center of the light-receiving means 2 is usually about 1 to 3 mm because the region from the skin surface to the microcirculation system is the subject of measurement.

When the optical properties for the skin S are measured with this apparatus, the edge 3b of the outer tube of the light-projecting and light-receiving probe 3 is brought into contact with the skin S, and the facing surface 1a of the light-projecting means 1 and the facing surface 2a of the light-receiving means 2 formed inside the light-projecting and light-receiving probe 3 are brought into contact with the skin S. The facing surface 1a is thus brought into contact with the skin, light from the light-projecting means 1 is projected onto the skin S, thereby making it possible to prevent the projected light that is scattered by the unevenness of the skin from being received by the light-receiving means 2, to increase the amount of light incident on the interior of the skin S from the light-projecting means 1, and to control fluctuations in the amount of incident light due to the angle of projection. The scattered light on the surface of the skin can be prevented from being received by bringing the facing surface 2a of the light-receiving means 2 into contact with the skin S. This apparatus thus allows only the internal scattered light to be received, while blocking out the scattered light on the surface of the skin, from among the light projected from the light-projecting means 1 onto the skin S, so the S/N can be improved when the amount of light having the prescribed wavelength is detected based on the content of melanin, hemoglobin, or the like in the region from the skin surface to the microcirculation system.

As described above, when the edge 3b of the light-projecting and light-receiving probe 3 is brought into contact with the skin S during measurement, the surface 1a of the light-projecting means 1 that faces the skin S or the surface 2a of the light-receiving means 2 that faces the skin S is surrounded by the peripheral wall 3a of the light-projecting and light-receiving probe 3, and is depressed about 0.2 to 0.8 mm from the edge 3b, so the optical properties of the skin S reflecting the influence of the microcirculation system can be accurately measured without excluding the blood from the microcirculation system at the measuring location of the skin S by being pressed by the light-projecting means 1 or light-receiving means 2.

EXAMPLES

The present invention is described in detail below based on examples.

Comparative Example 1 and Example 1

Pigmentation was induced by six differing dosages of fast skin-darkening UVB (wavelength 290 to 320 nm) radiation on the inner forearm (lightness index measurement value L* using spectral color difference meter (CM-1000, by Minolta) was 62.383, 61.348, 61.05, 58.853, 57.183, and 56.892), measurements were taken at these differing dosages, and the melanin index was determined.

Here, in Comparative Example 1, a Mexameter MX-16 by Courage & Knazaka was used as the instrument to receive the reflected light. The measuring instrument used in Comparative Example 1 comprised a light-emitting diode LED as the light source, wherein 568, 660, and 880 nm wavelength light was projected onto the skin without bringing the instrument into contact with the skin, and the light-receiving means detected both the internal scattered light and the surface reflected light projected from the light-projecting means onto the samples.

The apparatus illustrated in FIG. 4 was used as the measuring instrument in Example 1. The light projected from the light-projecting means in this case, however, had wavelengths G (660 nm) and R (830 nm).

The melanin index was determined by the following equation based on a method of calculating the melanin index with the MX-16.

$$\text{Melanin index} = \text{Log}5 \times \{\text{Log}(R/G) + \text{Log}5\} \times 500$$

(where R and G are the intensity of received light at wavelengths G (660 nm) and R (830 nm).) The results are given in FIG. 6 (Example 1) and FIG. 7 (Comparative Example 1).

Figure 6:
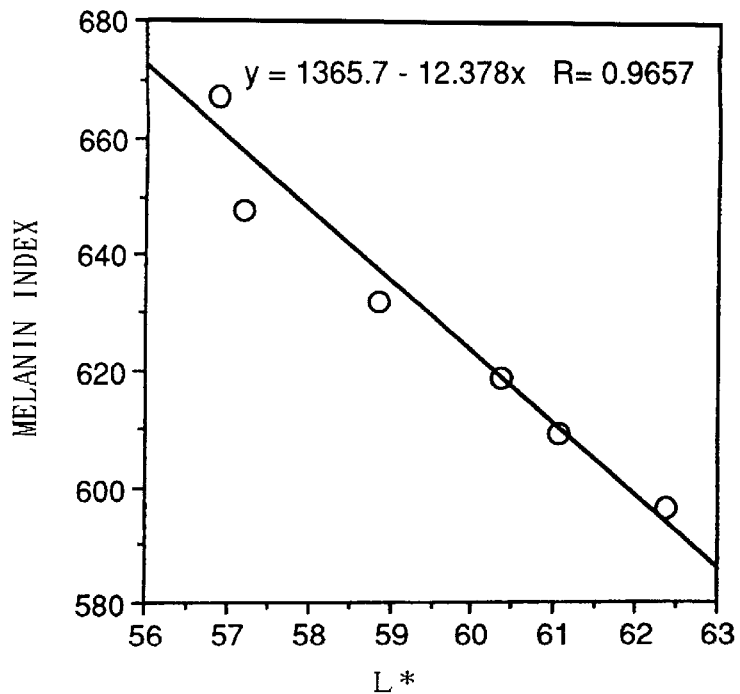
FIG. 6 illustrates the relation between the brightness index L* and the melanin index in an example of the present invention.
Figure 7:
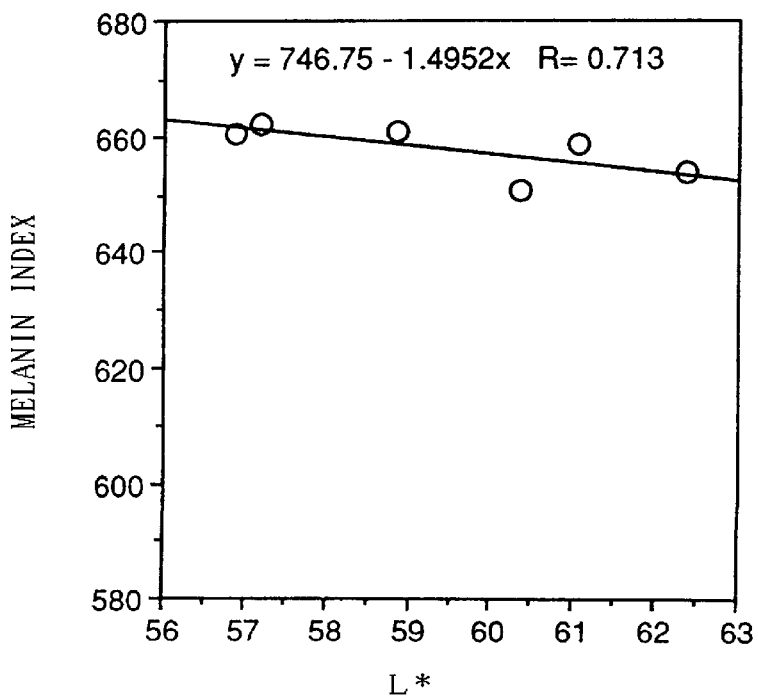
FIG. 7 illustrates the relation between the brightness index L* and the melanin index in a comparative example.

In FIGS. 6 and 7, greater UVB dosages resulted in stronger pigmentation and lower brightness measurement values L* by the spectral color meter, but it may be seen that the correlation coefficient R was higher in the results for the detection of internal scattered light in FIG. 6 for Example 1, and that the slope of the primary recurrence formula was greater. It may accordingly be seen that the measurement in Example 1 to detect the internal scattered light was more precise and sensitive than the measurement in Comparative Example 1 for detecting the scattered light on the surface.

Example 2

Changes in the compression time and blood condition were studied when the arm was compressed at maximum blood pressure (220 mmHg) and beyond.

Here, the detection wavelengths were 560, 660, and 830 nm, the oxygenated hemoglobin concentration and reduced hemoglobin concentration were calculated based on Equations (4) and (5), and the total hemoglobin concentration and hemoglobin oxygen saturation were determined.

Figure 8:
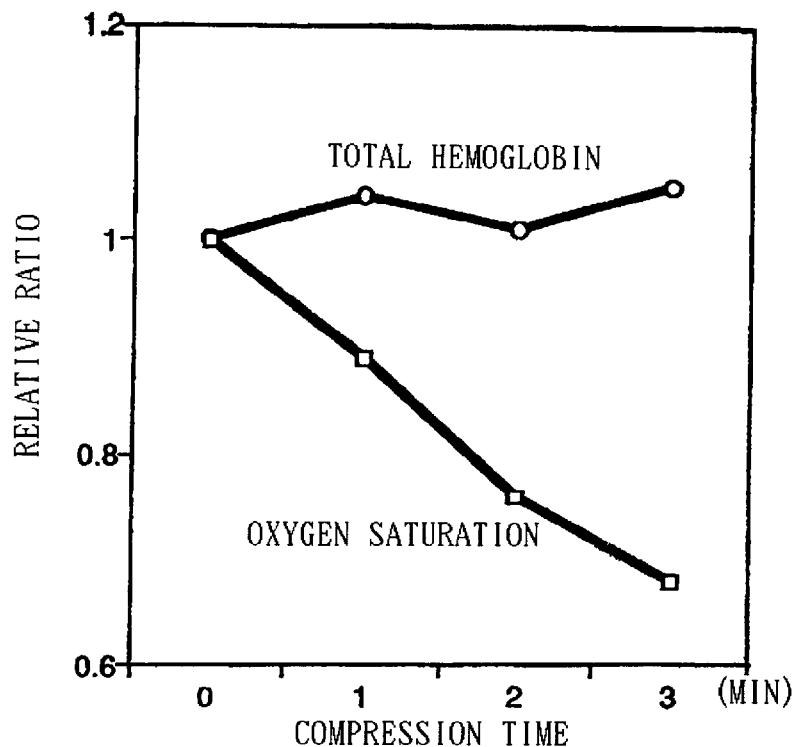
FIG. 8 illustrates the relation between compression time and total hemoglobin concentration or oxygen saturation.

For the coefficients relating to light depth, m=1.7 and n=3.2 in this example (these values vary according to differences in location and individual differences, and are not limited to those used in the present example). The brightness L* was measured using a spectral color difference meter (CM-100 by Minolta). The results are given in FIG. 8 and Table 1. In FIG. 8, the horizontal axis represents the compression time, and the vertical axis represents the relative values for total hemoglobin concentration and hemoglobin oxygen saturation starting when their values at compression starting time are regarded 1, respectively.

TABLE 1

| Compression time (min) | Brightness L* |
|---|---|
| 0 | 61.9 |
| 1 | 61.4 |
| 2 | 61.0 |
| 3 | 60.7 |

It may be seen from FIG. 8 that there were fewer changes over time in the total hemoglobin concentration, whereas th oxygen saturation decreased significantly over time. This is because the blood flow in both arteries and veins has stopped, and the oxygen was consumed while the amount of blood remained the same. The skin brightness also fell considerably at this time. It may thus be seen that not only is it important to measure the total hemoglobin concentration but also to determine the oxygen saturation in order to achieve more detailed evaluation of the effect of the microcirculation system blood on skin color.

When two detection wavelengths are used, the total hemoglobin concentration can be determined by using absorption points where the absorption coefficients of oxygenated and reduced forms of hemoglobin are equivalent, but the oxygen saturation cannot be calculated in principle without reference to absorbance at wavelengths other than absorption points where they are equivalent. As such, at least three wavelengths are used as detection wavelengths, as in this example, to determine the oxygen saturation.

Example 3

The skin color indices of the cheeks of 103 women subjects ranging from 20 to 70 years of age were determined from absorbance measurements based on the internal scattered light at the three wavelengths of B (400 to 500 nm), G (500 to 600 nm), and R (600 to 800 nm). The sensory test of skin color of these samples was practiced by a panel of 9 experts based on 9 ranks from 1 (poor) to 9 (good), and the relation between the results of the sensory test and the skin color index was plotted. The results are given in FIG. 9.

Figure 9:
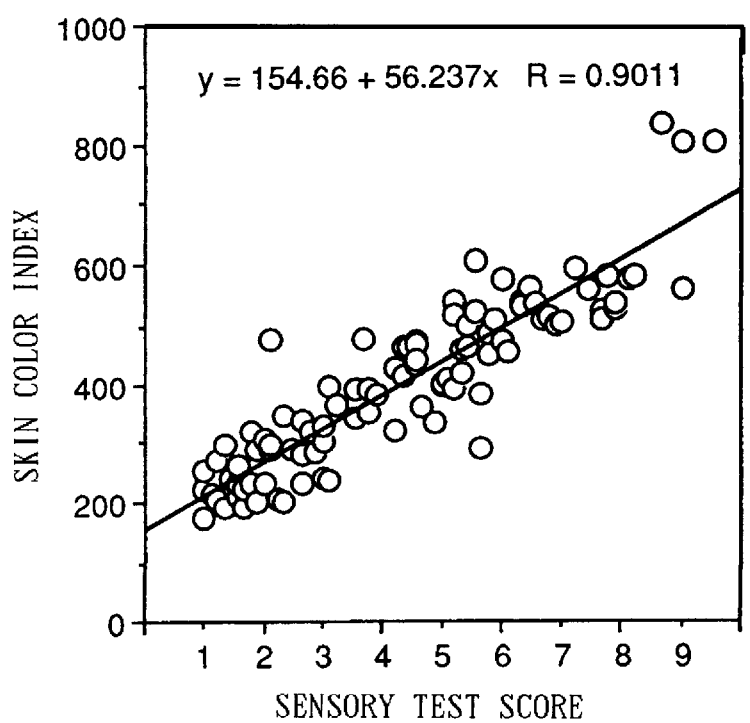
FIG. 9 illustrates the relation between sensory test scores and the skin color index based on example.

FIG. 9 shows a good correlation between the skin color index of the present invention and the results of the sensory test by the expert panel.

What is claimed is:

1. A method for measuring optical properties of a surface state of skin comprising applying light on said skin, detecting internal scattered light in a region from said skin surface to the microcirculation system and determining said optical properties.

2. The measuring method according to claim 1, wherein light-projecting means is brought into contact with the skin to allow light to be applied thereon, and light-receiving means is brought into contact with the skin to receive the internal scattered light in the skin.

3. The measuring method according to claim 1, wherein light is detected at a wavelength of between 400 and 1500 nm.

4. The measuring method according to claim 1, wherein light is detected at a wavelength between 400 and 500 nm.

5. The measuring method according to claim 1, wherein light is detected at a wavelength between 500 and 600 nm.

6. The measuring method according to claim 1, wherein light is detected at a wavelength between 600 and 800 nm.

7. The measuring method according to claim 1, wherein light is detected at a wavelength between 800 and 1500 nm.

8. The measuring method according to claim 1, wherein light is detected in at least three wavelength regions.

9. The measuring method according to claims 8, wherein the optical properties are determined based on the hemoglobin content of the skin, the oxygen saturation of the hemoglobin and the melanin content of the skin.

10. The measuring method according to claims 8, wherein a skin color index of the skin is determined.

11. An apparatus for measuring the surface state of the skin comprising light-projecting means for applying light having a specific wavelength region skin; light-receiving means for receiving a internal scattered light of a light applied on the skin from the light-projecting means; and computing means for computing the optical properties of the skin in the region from the skin surface to the microcirculation system based on the wavelength and amount of light received by the light-receiving means, wherein the surfaces of said light-projecting means and said light-receiving means facing the skin are surrounded by a 0.2 to 0.8 mm high peripheral wall.

12. The measuring apparatus according to claim 11, wherein the light-projecting means applies light on the skin in at least three wavelength regions.

* * * * *